United States Patent [19]

Mendiratta et al.

[11] Patent Number: 4,492,806

[45] Date of Patent: Jan. 8, 1985

[54] PROCESS FOR PREPARING ALKALI METAL SALTS OF HYDROXYAROMATIC COMPOUNDS

[75] Inventors: Ashok K. Mendiratta, Schenectady; Wayne F. Morgan, Mechanicville, both of N.Y.

[73] Assignee: General Electric Company, Schenectady, N.Y.

[21] Appl. No.: 555,752

[22] Filed: Nov. 28, 1983

[51] Int. Cl.$^3$ ............................................. C07C 39/16
[52] U.S. Cl. .................................... 568/723; 568/716
[58] Field of Search ................................. 568/723, 716

[56] References Cited

U.S. PATENT DOCUMENTS

| | | | |
|---|---|---|---|
| 3,554,265 | 1/1971 | Milan | 568/716 |
| 3,960,968 | 6/1976 | Vernaleken et al. | 568/723 |
| 3,974,084 | 8/1976 | Pietzch et al. | 568/716 |
| 4,257,953 | 3/1981 | Williams | 568/722 |
| 4,302,616 | 11/1981 | Williams | 568/722 |
| 4,410,736 | 10/1983 | Dellacoletta | 568/730 |

*Primary Examiner*—Werren B. Lone
*Attorney, Agent, or Firm*—William H. Pittman; James C. Davis, Jr.; James Magee, Jr.

[57] ABSTRACT

Anhydrous alkali metal (especially sodium) salts of hydroxyaromatic compounds, particularly bisphenols such as bisphenol A, are prepared by forming a solution of the hydroxyaromatic compound in a solvent mixture comprising a relatively high boiling non-polar organic liquid such as toluene or o-dichlorobenzene and an alkanol containing up to about 4 carbon atoms, preferably methanol; contacting said solution with an aqueous solution of a substantially stoichiometric amount of alkali metal hydroxide; and removing substantially all volatile materials from the reaction mixture by evaporation. The product thus obtained is a slurry of the anhydrous alkali metal salt in the non-polar liquid.

15 Claims, No Drawings

PROCESS FOR PREPARING ALKALI METAL SALTS OF HYDROXYAROMATIC COMPOUNDS

This invention relates to the preparation of alkali metal salts of hydroxyaromatic compounds and to a method of recovery thereof.

The preparation of alkali metal salts of hydroxyaromatic compounds, especially dihydroxyaromatic compounds such as bisphenol A, typically and conveniently takes place in an aqueous system. Many commercially important reactions of said salts, however, such as their reaction with nitrophthalimides to form aromatic ether imides, are best carried out under anhydrous conditions to maximize yields. It is necessary, therefore, to isolate the salt in anhydrous form.

Various methods for removal of water from such salts have been disclosed. For example, U.S. Pat. No. 4,202,993 describes a flash evaporation method, while U.S. Pat. No. 4,257,953 discloses azeotropic distillation of the water using a hydrocarbon solvent such as toluene. While these methods are effective, they suffer from certain disadvantages. For example, large expenditures of time and energy (including a high thermal history) and multiple treatment vessels are required, and the alkali metal salt is susceptible to caking during the removal of water.

A principal object of the present invention, therefore, is to provide an improved process for the preparation of alkali metal salts of hydroxyaromatic compounds.

A further object is to provide an improved method for the removal of water from such salts.

A further object is to provide a method for recovery of such salts in anhydrous form as free-flowing solids, adapted for easy handling during further reactions.

A still further object is to prepare such salts by a method involving a single vessel, minimum energy expenditure including low thermal history, and more economical processing time.

Other objects will in part be obvious and will in part appear hereinafter.

In its broadest sense, the present invention is directed to a method for preparing at least one anhydrous alkali metal salt of a hydroxyaromatic compound which comprises:

(A) forming a solution of at least one hydroxyaromatic compound in a solvent mixture comprising (I) a major proportion of at least one substantially inert and substantially non-polar organic liquid which has a boiling point higher than that of water or which forms an azeotrope with water, and (II) a minor proportion of at least one alkanol containing up to about 4 carbon atoms, said alkanol being capable of removal by evaporation from the combination of said solvent mixture with water;

(B) contacting said solution with an aqueous solution of a substantially stoichiometric amount of alkali metal hydroxide for a period of time sufficient to form said alkali metal salt; and (C) removing substantially all volatile materials, including water and said liquid II, from the reaction mixture by evaporation, thereby obtaining a slurry in said liquid I of said anhydrous alkali metal salt.

The hydroxyaromatic compounds which may be converted to alkali metal salts according to the method of this invention generally have the formula $Z(OH)_n$, wherein Z is an aromatic radical and n is 1 or 2. Such compounds include phenol, o-cresol, m-cresol, p-cresol, 1-naphthol, 2-naphthol, p-chlorophenol, catechol, resorcinol, resorcinol monomethyl ether, hydroquinone, biphenol, bis(4-hydroxyphenyl)methane and bisphenol A, or 2,2-bis(4-hydroxyphenyl)propane.

In a preferred embodiment of the invention, the value of n is 2 and Z has one of the following formulas:

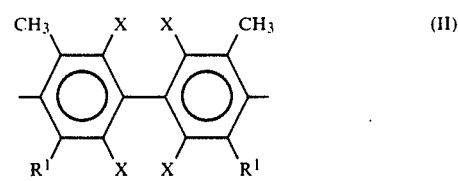

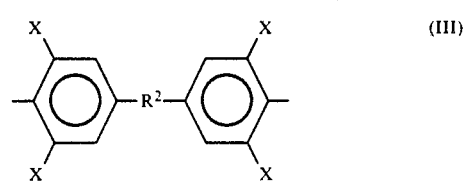

In these formulas, each $R^1$ is independently hydrogen or methyl, $R^2$ is a straight-chain or branched alkylene radical containing 1–5 carbon atoms and is most often the isopropylidene radical, and each X is independently hydrogen or halogen (usually chlorine or bromine). The compounds in which Z has formula III are bisphenols. Since the invention is particularly useful for the preparation of bisphenol salts, frequent reference to bisphenols will be made hereinafter. The preferred bisphenol is bisphenol A, which has formula III wherein $R^2$ is isopropylidene and each X is hydrogen.

The alkali metal salts which are formed by the method of this invention are those of the metals of Group IA of the periodic table; namely, lithium, sodium, potassium, rubidium and cesium. For reasons of economy and availability, the sodium and potassium satls, especially the former, are preferred.

In step A of the method of this invention, the bisphenol is dissolved in a solvent mixture comprising at least two components. Liquid I, present in major proportion, is at least one substantially inert (under the conditions of the invention) and substantially non-polar organic liquid which either has a boiling point higher than that of water (i.e., higher than 100° C.) or forms an zeotrope with water. These conditions are applicable because a liquid which has a lower boiling point than water and does not form an azeotrope therewith will be removed by evaporation during step C before the water is removed.

Typical organic liquids which may be used as liquid I include benzene, toluene, xylene, chlorobenzene, o-dichlorobenzene, heptane, octane, nonane, decane, petroleum naphthas with a higher boiling point than that of water, chloroform and carbon tetrachloride. While the degree of solubility of water in the organic liquid is not critical, operation such as product recovery and liquid recycle are optimized when liquid I is one in which water is substantially insoluble and which boils above 105° C. and preferably below about 200° C., and especially one in which the bisphenol sodium salt is substantially insoluble. The aromatic hydrocarbons and halogenated (most often chlorinated) hydrocarbons (e.g., benzene, toluene, xylene, chlorobenzene, o-dichlorobenzene) are especially suitable; of these, toluene and o-dichlorobenzene are most desirable because of their effectiveness, availability and relatively low price.

Liquid II, present in minor proportion, is at least one alkanol containing up to about 4 carbon atoms. Alkanols included within this geneous are methanol, ethanol, 1-propanol, 2-propanol, 1-butanol, 2-butanol (sec-butyl alcohol), 2-methyl-1-propanol (isobutyl alcohol) and 2-methyl-2-propanol (tert-butyl alcohol). In general, the primary alkanols are preferred.

Liquid II must also be capable of removal by evaporation from the combination of the solvent mixture with water. Thus, the suitability of various alkanols will depend to some extent on the identity of liquid I and the temperature at which water is removed by evaporation from the water-solvent mixture combination. Methanol and ethanol are capable of removal under virtually all conditions of operation of the method of this invention, and they are preferred for use as liquid II, with methanol being especially preferred.

The principal function of liquid II in step A is to solubilize the bisphenol in the solvent system. Its presence for this purpose is usually necessary since bisphenols are not sufficiently soluble in substantially nonpolar organic liquids to form a homogeneous solution. In later stages of the method of this invention, liquid II performs other functions as described hereinafter.

The weight ratio of liquid I to liquid II required for such solubilization will vary according to the particular reagents and reaction conditions employed. It is frequently from about 4:1 to about 8:1 and preferably from about 4.5:1 to about 6:1. The weight percentage of the bisphenol in the solvent mixture may generally be about 5–30%; it is usually about 5–15% and preferably about 8–12%.

In step B, the solution obtained in step A is contacted with an aqueous solution of alkali metal hydroxide, preferably sodium hydroxide. A solution containing about 30–70% by weight of the alkali metal hydroxide is generally suitable. Solutions of about 50% concentration are readily available and their use is particularly preferred. Contact during step B may typically be effected at a temperature within the range of about 40°–100° C., preferably about 50°–55° C., and for a period of time sufficient to form the desired alkali metal salt. In general, contact for about 1.5–3 hours is sufficient.

The amount of alkali metal hydroxide used in step B is substantially stoichiometric; that is, about 1 equivalent of alkali metal hydroxide is used per equivalent of hydroxyaromatic compound. For the purpose of this invention, the equivalent weight of the hydroxyaromatic compound is its molecular weight divided by the number of aromatic hydroxy groups therein. In order to insure completion of the reaction, it may be desirable to use an excess of alkali metal hydroxide. However, according to the present invention any such excess will remain in the product since no steps for its removal are included. The presence of alkali metal hydroxide during the reaction of the bisphenol alkali metal salt with a nitrophthalimide is undesirable. When the product is to be used for this or a similar purpose, therfore, any excess of alkali metal hydroxide should be maintained below about 0.1 mole percent and preferably below about 0.05 mole percent.

During step B, liquid II continues to perform the function of solubilizing the bisphenol in the reaction mixture. At this stage, however, it also insures that any bisphenol alkali metal salt which precipitates is in fine crystalline form. In the absence of liquid II the amount of water present in the reaction mixture must be increased to maintain the bisphenol in solution, and this causes caking of the alkali metal salt during drying and also increases the energy input required for removal of said water in later stages of the process.

In step C, substantially all volatile materials, including water and liquid II, are removed from the reaction mixture by evaporation. The evaporative process used may be flash evaporation, distillation or any other suitable type. Often, a portion of liquid I is simultaneously removed by evaporation, especially when it forms an azeotrope with water, but evaporation of liquid I is not an essential feature of the method. When liquid I is a water-immiscible liquid such as toluene, it is frequently convenient to recycle it to step A or to introduce additional amounts thereof at an elevated temperature, typically about 100° C., continuously or intermittently until the condensate no longer contains a substantial amount of volatile materials. Typically, drying is complete when said condensate contains less than about 100 ppm. and preferably less than about 50 ppm. of water.

Following step C, the dry anhydrous alkali metal salt may be separated from the organic liquid. In the preferred embodiment of the invention which employs as liquid I a liquid in which the anhydrous salt is substantially insoluble, separation is relatively simple and may be effected by filtration, centrifugation or the like. Remaining traces of organic liquid in the salt may be removed by vacuum drying or a similar operation. It is, however, often most convenient to employ the salt in slurry form. An illustration is its reaction with a nitrophthalimide. For such uses, separation of the salt from the organic liquid is unnecessary.

The method of this invention has many advantages over previously known processes involving such expedients as azeotropic removal of all the water in which the alkali metal salt was dissolved. In the first place, according to the method of this invention the water in the system is removed relatively simply in step C, with minimum thermal history and low time requirement. In the second place, the anhydrous salt is obtained as a free-flowing solid with little or no tendency to agglomerate or cake. In the third place, the entire procedure can be effected in a single reaction vessel, typically a stirred tank reactor, without the need for relatively complex operations such as filtration or spray drying. In the fourth place, the method can be adapted for continuous operation.

The invention is illustrated by the following examples. All parts are by weight.

EXAMPLE 1

A reaction vessel was charged with 50 parts (0.44 equivalent) of bisphenol A, 400 parts of toluene and 80 parts of methanol, thereby forming a homogeneous solution at 55° C. There was added at 55° C. over 5 minutes, with stirring, 35.1 parts of a 50% (by weight) aqueous sodium hydroxide solution (0.44 equivalent of sodium hydroxide). Stirring was continued at 55° C. for 2 hours, after which analysis of the reaction mixture showed only trace amounts of bisphenol A remaining.

The temperature of the reaction vessel was increased to 130° C. and volatiles were removed by distillation, with fresh hot toluene being added periodically to maintain a constant liquid level. At the end of 2½ hours of distillation, the condensate showed the presence of only 50 ppm. of water. The mixture in the reaction vessel was a toluene slurry of the desired disodium salt of bisphenol A, free from water and methanol. The salt therein was in finely divided form with no lumps or cakes.

EXAMPLE 2

The procedure of Example 1 is repeated, except that o-dichlorobenzene is substituted for the toluene. The disodium salt of bisphenol A is obtained in finely divided form as a slurry in o-dichlorobenzene.

What is claimed is:

1. A method for preparing at least one anhydrous alkali metal salt of a hydroxyaromatic compound which comprises:
    (A) forming a solution of at least one hydroxyaromatic compound in a solvent mixture comprising (I) a major proportion of at least one substantially non-polar organic liquid which has a boiling point higher than that of water or which forms an azeotrope with water, and (II) a minor proportion of at least one alkanol containing up to about 4 carbon atoms, said alkanol being capable of removal by evaporation from the combination of said solvent mixture with water; the weight ratio of liquid I to liquid II being from 4:1 to about 8:1;
    (B) reacting said solution at a temperature within the range of about 40°-100° C. with an aqueous solution of a substantially stoichiometric amount of alkali metal hydroxide for a period of time sufficient to form said alkali metal salt; and
    (C) removing substantially all volatile materials, including water and said liquid II, from the reaction mixture by evaporation, thereby obtaining a slurry in said liquid I of said anhydrous alkali metal salt.

2. A method according to claim 1 wherein the alkali metal is sodium.

3. A method according to claim 2 wherein the hydroxyaromatic compound is a bisphenol.

4. A method according to claim 3 wherein step B is effected at a temperature within the range of about 40°-60° C.

5. A method according to claim 4 wherein liquid I is one in which water is substantially insoluble and which boils in the range of about 105°-200° C.

6. A method according to claim 5 wherein liquid II is a primary alkanol.

7. A method according to claim 6 wherein the sodium hydroxide solution in step B contains about 30-70% by weight of sodium hydroxide.

8. A method according to claim 7 wherein liquid II is methanol or ethanol.

9. A method according to claim 8 wherein liquid I is toluene or o-dichlorobenzene.

10. A method according to claim 9 wherein liquid I is toluene and liquid II is methanol.

11. A method according to claim 6 wherein the hydroxyaromatic compound is bisphenol A.

12. A method according to claim 11 wherein the sodium hydroxide solution in step B contains about 30-70% by weight of sodium hydroxide.

13. A method according to claim 12 wherein liquid II is methanol or ethanol.

14. A method according to claim 13 wherein liquid I is toluene or o-dichlorobenzene.

15. A method according to claim 14 wherein liquid I is toluene and liquid II is methanol.

* * * * *